(12) United States Patent
Geng et al.

(10) Patent No.: US 8,178,485 B2
(45) Date of Patent: May 15, 2012

(54) HEXAHYDRO ETHANOCHROMENES AND RELATED COMPOUNDS AND THEIR USE IN FRAGRANCE COMPOSITIONS

(75) Inventors: Feng Geng, Piscataway, NJ (US); Richard M. Boden, Ocean, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 163 days.

(21) Appl. No.: 12/855,049

(22) Filed: Aug. 12, 2010

(65) Prior Publication Data

US 2012/0041214 A1 Feb. 16, 2012

(51) Int. Cl.
*A61K 8/49* (2006.01)
*C11D 3/50* (2006.01)
*C07D 311/78* (2006.01)

(52) U.S. Cl. ............................ 512/13; 510/103; 549/386

(58) Field of Classification Search ................... 549/386; 512/13; 510/103
See application file for complete search history.

(56) References Cited

U.S. PATENT DOCUMENTS 7,446,080 B2 * 11/2008 Narula et al. ................ 510/103
* cited by examiner

*Primary Examiner* — Bernard Dentz
(74) *Attorney, Agent, or Firm* — Elizabeth M. Quirk; XuFan Tseng; Joseph F. Leightner

(57) ABSTRACT

The present invention relates to novel compounds and their use in fragrance compositions. Novel hexahydro ethanochromene and related hexahydro ethanochromane compounds of the present invention are represented by formula:

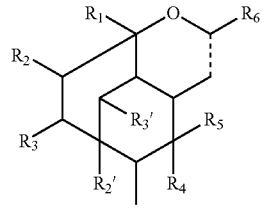

wherein $R_1$ is hydrogen or methyl; $R_2$ and $R_2'$ are identical and are hydrogen or methyl; $R_3$ and $R_3'$ are identical and are hydrogen or methyl; $R_4$ and $R_5$ are independently hydrogen or methyl; $R_6$ is methyl, ethyl, or isopropyl, with the proviso that when $R_1$ is H, $R_2$ and $R_3'$ form an alkylene bridge containing 1 or 2 carbon atoms, and wherein the broken line represents a single or double bond.

17 Claims, No Drawings

HEXAHYDRO ETHANOCHROMENES AND RELATED COMPOUNDS AND THEIR USE IN FRAGRANCE COMPOSITIONS

FIELD OF THE INVENTION

The present invention relates to new chemical entities and their incorporation and use as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in chemical structures can result in significant differences in odor, notes and characteristics of molecules. These variations allow perfumers and other persons to apply new compounds in creating new fragrances.

SUMMARY OF THE INVENTION

The present invention provides novel compounds and their unexpected advantageous use in enhancing, improving or modifying the fragrance of perfumes, colognes, toilet waters, fabric care products, personal products, and the like.

Specifically, one embodiment of the invention relates to novel hexahydro ethanochromene and related hexahydro ethanochromane compounds represented by Formula Ia set forth below:

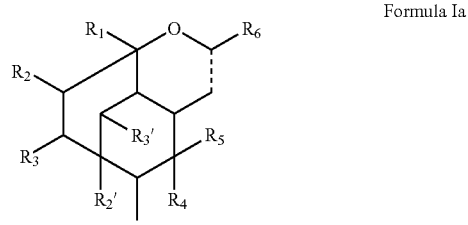

Formula Ia wherein $R_1$ is selected from the group consisting of hydrogen and methyl;

$R_2$ and $R_2'$ are identical and are selected from the group consisting of hydrogen and methyl;

$R_3$ and $R_3'$ are identical and are selected from the group consisting of hydrogen and methyl;

$R_4$ and $R_5$ are independently selected from the group consisting of hydrogen and methyl; and $R_6$ is selected from the group consisting of methyl, ethyl, and isopropyl, with the proviso that when $R_1$ is H, $R_2$ and $R_3'$ form an alkylene bridge containing 1 or 2 carbon atoms, and wherein the broken line represents a single or double bond.

Another embodiment of the invention relates to novel hexahydro ethanochromene and related hexahydro ethanochromane compounds represented by Formula Ib set forth below:

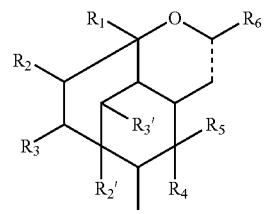

Formula Ib wherein $R_1$ is methyl;

$R_2$ and $R_2'$ are identical and are selected from the group consisting of hydrogen and methyl;

$R_3$ and $R_3'$ are identical and are selected from the group consisting of hydrogen and methyl;

$R_4$ and $R_5$ are independently selected from the group consisting of hydrogen and methyl; and $R_6$ is selected from the group consisting of methyl, ethyl, and isopropyl, and wherein the broken line represents a single or double bond.

Another embodiment of the invention relates to a fragrance composition comprising a hexahydro ethanochromene or a hexahydro ethanochromane compound represented by Formulas Ia and Ib provided above.

Another embodiment of the invention relates to a method of improving, enhancing or modifying a fragrance formulation through the addition of an olfactory acceptable amount of a hexahydro ethanochromene or a hexahydro ethanochromane compound represented by Formulas Ia and Ib provided above.

These and other embodiments of the present invention will be apparent by reading the following specification.

DETAILED DESCRIPTION OF THE INVENTION

In Formulae Ia above, $R_1$ is hydrogen or methyl; $R_2$ and $R_2'$ are identical and are hydrogen or methyl; $R_3$ and $R_3'$ are identical and are hydrogen or methyl; $R_4$ and $R_5$ are independently hydrogen or methyl; $R_6$ is methyl, ethyl, or isopropyl, with the proviso that when $R_1$ is H, $R_2$ and $R_3'$ form an alkylene bridge containing 1 or 2 carbon atoms, and the broken line represents a single or double bond.

In Formula Ib above, $R_1$ is methyl; $R_2$ and $R_2'$ are identical and are hydrogen or methyl; $R_3$ and $R_3'$ are identical and are hydrogen or methyl; $R_4$ and $R_5$ are independently hydrogen or methyl; $R_6$ is methyl, ethyl, or isopropyl, and the broken line represents a single or double bond.

In one embodiment of the invention, the novel compounds of the present invention are represented by the following structures:

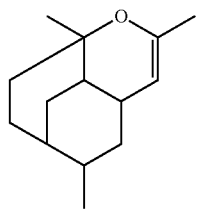

Structure I

Structure II

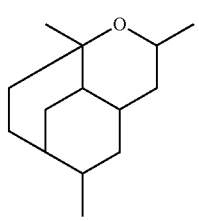

Those with the skill in the art will appreciate that Structure I is 4,6,11-trimethyl-5-oxa-tricyclo[6.2.2.0*4,9*]dodec-6-ene and Structure II is 4,6,11-trimethyl-5-oxa-tricyclo[6.2.2.0*4,9*]dodecane.

Novel hexahydro ethanochromene and related hexahydro ethanochromane compounds of the present invention can be prepared from suitable 3-(cyclohex-3-enyl)-butyraldehydes according to a general reaction scheme shown as follows:

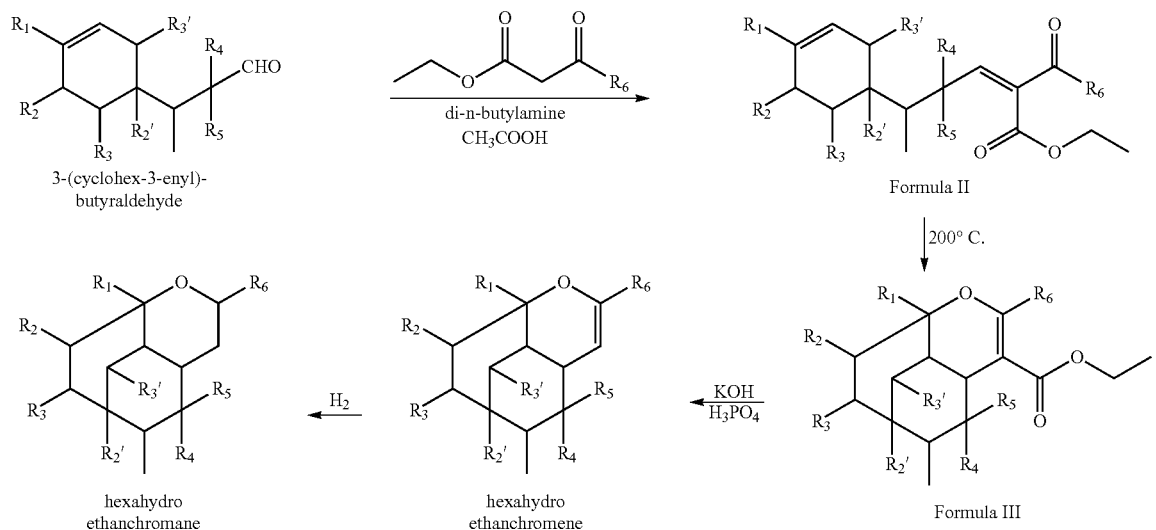

Those with skill in the art will recognize that the compounds of the present invention may have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The compounds of the present invention are surprisingly found to possess woody, powdery, floral, and sweet notes. In particular, when used in combination with other fragrance materials, the compounds of the present invention unexpectedly intensify and substantiate the top notes, such as providing and/or enhancing the fresh, citrus, floral, and green notes for the other fragrance materials.

The use of the compounds of the present invention is widely applicable in current perfumery products, including the preparation of perfumes and colognes, the perfuming of personal care products such as soaps, shower gels, and hair care products, fabric care products as well as air fresheners and cosmetic preparations. These compounds can also be used to perfume cleaning agents, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like. A list of suitable fragrances is provided in U.S. Pat. No. 4,534,891, the contents of which are incorporated by reference as if set forth in its entirety. Another source of suitable fragrances is found in Perfumes, Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory acceptable amount is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compounds of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation may vary from about 0.005 to about 70 weight percent, preferably from 0.05 to about 35 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation, the compounds of the present invention unexpectedly intensity and substantiate the fresh, citrus, floral, and green characteristics and make the fragrance formulation more desirable and noticeable. The compounds of the present invention assist in beautifying and enhancing the finished accord and improve the performance of other materials in the fragrance formulation.

The following are provided as specific embodiments of the present invention. Other modifications of this invention will be readily apparent to those skilled in the art. Such modifications are understood to be within the scope of this invention. All reagents were purchased from Sigma-Aldrich, Inc. unless otherwise noted. Further, as used herein all percentages are weight percent unless otherwise noted, L is understood to be liter, g is understood to be gram, Kg is understood to be kilogram, and mmHg be millimeters (mm) of mercury (Hg). IFF as used in the examples is understood to mean International Flavors & Fragrances Inc., New York, N.Y., USA.

Example I

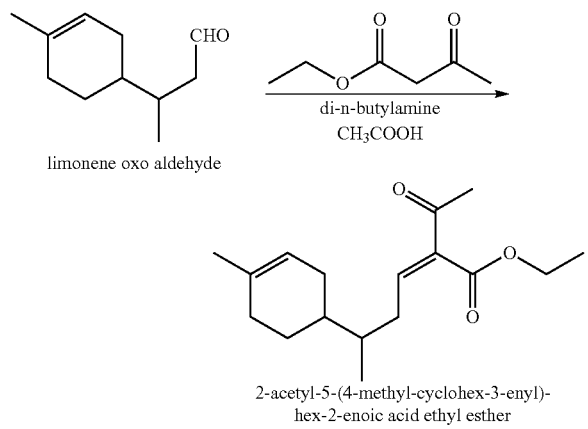

Preparation of 2-Acetyl-5-(4-methyl-cyclohex-3-enyl)-hex-2-enoic acid ethyl ester: A 12 L three-neck flask equipped with a condenser, a mechanic stirrer, and a thermometer was charged with toluene (2 L), di-n-butylamine (232 g), acetic acid ($CH_3COOH$, 108 g), and limonene oxo aldehyde (3 Kg, commercially available from IFF). The reaction mixture was kept below 20° C. using an ice-water bath. Ethyl acetoacetate (2.35 Kg) was then added over 1 hour period. After aging for another hour, gas chromatographic (GC) analysis indicated the reaction was completed. The reaction mixture was washed sequentially with aqueous hydrochloric acid (10%, 1 L), water ($H_2O$, 1 L), saturated aqueous sodium bicarbonate ($NaHCO_3$, 2 L), and $H_2O$ (1 L). A small sample of the resulting material was purified via Silica gel chromatography for analysis. The resulting material was a solution of 2-acetyl-5-(4-methyl-cyclohex-3-enyl)-hex-2-enoic acid ethyl ester in toluene (7.4 L).

$^1$H NMR ($CDCl_3$): δ 0.87-1.05 (m, 3H); 1.13-1.47 (m, 5H); 1.63 (s, 3H); 1.56-1.82 (m, 2H); 1.86-2.06 (br, 3H); 2.06-2.28 (m, 2H); 2.30-2.57 (m, 1H); 2.31 (s, 61% of 3H); 2.36 (s, 39% of 3H); 4.08-4.35 (m, 2H); 5.36 (br, 1H); 6.85-6.90 (m, 61% of 1H); 6.97-6.92 (m, 39% of 1H).

Example II

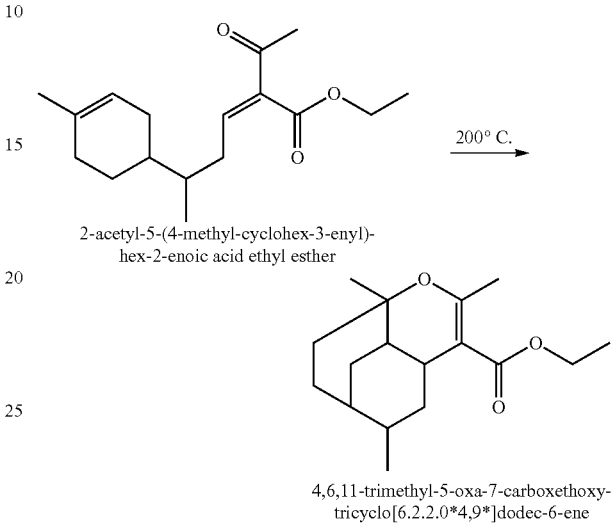

Preparation of 4,6,11-Trimethyl-5-oxa-7-carboxethoxy-tricyclo[6.2.2.0*4,9*]dodec-6-ene: A 6 L three-neck flask equipped with a thermometer, a mechanic stirrer, and a Dean-Stark trap was charged with a solution of 2-acetyl-5-(4-methyl-cyclohex-3-enyl)-hex-2-enoic acid ethyl ester in toluene (4.3 L, obtained as above). The solution was heated to 200° C., during which process toluene and other volatile materials were collected through the Dean-Stark Dean-Stark trap and removed. The remaining material was maintained at 200° C. for 80 minutes. GC analysis indicated that the reaction was completed. The reaction flask was then cooled to an ambient temperature. A small sample of the resulting material was purified via Silica gel chromatography for analysis. The resulting material was a crude product 4,6,11-trimethyl-5-oxa-7-carboxethoxy-tricyclo[6.2.2.0*4,9*]dodec-6-ene (2.32 Kg).

$^1$H NMR ($CDCl_3$): δ 0.90 (~67% of 3H, d, J=6.82 Hz); 0.91-1.08 (m, 1H); 1.09 (~33% of 3H, d, J=7.23 Hz); 1.21-1.35 (m, 1H); 1.28 (m, 3H); 1.40 (2s, 3H); 1.51-2.06 (m, 8H); 2.14-2.20 (m, 1H); 2.20 (2s, 3H); 2.71-2.77 (~67% of 1H, m); 2.79-2.86 (~33% of 1H, m); 4.12-4.21 (m, 2H).

Example III

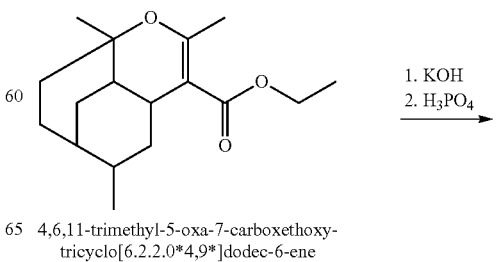

4,6,11-trimethyl-5-oxa-7-carboxethoxy-tricyclo[6.2.2.0*4,9*]dodec-6-ene

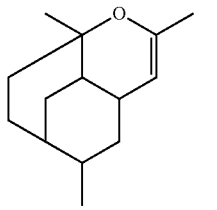

4,6,11-trimethyl-5-oxa-
tricyclo[6.2.2.0*4,9*]dodec-6-ene

Preparation of 4,6,11-Trimethyl-5-oxa-tricyclo[6.2.2.0*4, 9*]dodec-6-ene (Structure I): A 5 L three-neck flask equipped with a thermometer, a mechanic stirrer, a Dean-Stark trap, and a bubbler was charged with the crude product 4,6,11-trimethyl-5-oxa-7-carboxethoxy-tricyclo[6.2.2.0*4,9*]dodec-6-ene (1.665 Kg, obtained as above). Ethylene glycol (1.5 Kg) was added followed by the addition of potassium hydroxide (KOH, 560 g) with stirring. The reaction mixture was then heated to 140° C. and maintained at this temperature for 2 hours. GC analysis indicated the total consumption of the starting crude product. The reaction mixture was then cooled and poured slowly into a mixture of phosphoric acid ($H_3PO_4$, 1 Kg) and ice (2 Kg). The reaction mixture was stirred and the organic layer was separated. The aqueous layer was further extracted with toluene (500 mL). The organic layers were combined and charged back to the initial reaction set-up. The reaction mixture was heated to 130° C. and the solvent was collected via the Dean-Stark trap. After aging for 6 hours, the reaction was cooled to room temperature and washed sequentially with $H_2O$ (2 L), saturated $NaHCO_3$ (2 L), and $H_2O$ (2 L). The crude mixture was distilled to provide the product 4,6,11-trimethyl-5-oxa-tricyclo[6.2.2.0*4,9*]dodec-6-ene (645 g), which had a boiling point of 140° C. at a pressure of 0.9 mmHg $^1$H NMR ($CDCl_3$): δ 0.87 (~67% of 3H, d, J=6.72 Hz); 1.01 (~33% of 3H, d, J=7.14 Hz); 1.11 (m, 1H); 1.30 (2s, 3H); 1.31-1.58 (m, 4H); 1.61 (s, 3H); 1.61-2.21 (m, 7H); 4.44 (~33% of 1H, d, J=5.39 Hz); 4.47 (~67% of 1H, d, J=5.51 Hz).

4,6,11-Trimethyl-5-oxa-tricyclo[6.2.2.0*4,9*]dodec-6-ene was described as having woody, powdery, floral, and sweet notes.

Example IV

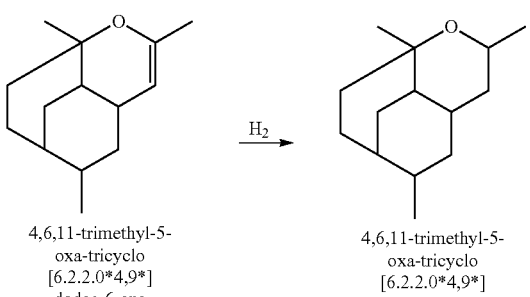

4,6,11-trimethyl-5-oxa-tricyclo[6.2.2.0*4,9*]dodec-6-ene 4,6,11-trimethyl-5-oxa-tricyclo[6.2.2.0*4,9*]dodecane Preparation of 4,6,11-Trimethyl-5-oxa-tricyclo[6.2.2.0*4, 9*]dodecane (Structure II): In an autoclave, 4,6,11-trimethyl-5-oxa-tricyclo[6.2.2.0*4,9*]dodec-6-ene (770 g, obtained as above) and palladium (5%, 7.6 g) on carbon was added to 2-propanol (100 g). The reaction mixture was stirred at a temperature between 70-100° C. under a pressure of 300 psi hydrogen for 6 hours. GC analysis indicated that the reaction was completed. The resulting material was then filtered and distilled under a reduced pressure to provide 4,6,11-trimethyl-5-oxa-tricyclo[6.2.2.0*4,9*]dodecane (720 g), which had a boiling point of 132° C. at a pressure of 0.8 mmHg $^1$H NMR ($CDCl_3$): δ 0.93 (~50% of 3H, d, J=6.82 Hz); 0.95-1.14 (m, 1H); 1.03 (~50% of 3H, d, J=7.24 Hz); 1.09 (d, 3H, J=6.07 Hz); 1.25 (2s, 3H); 1.31-2.13 (m, 13H); 3.80-3.89 (m, 1H).

4,6,11-Trimethyl-5-oxa-tricyclo[6.2.2.0*4,9*]dodecane was described as having woody and green notes.

Example V

The fragrance formulas exemplified as follows demonstrated that 4,6,11-trimethyl-5-oxa-tricyclo[6.2.2.0*4,9*]dodec-6-ene (Structure I) intensified and substantiated the top notes such as the fresh, citrus, floral, and green characteristics, and provided a fragrance formula that was more desirable and noticeable.

|  | Parts* | |
| --- | --- | --- |
| Ingredients | + | − |
| ALLYL AMYL GLYCOLATE BHT | 2.00 | 2.00 |
| AMBERIFF CRYST | 0.30 | 0.30 |
| BERGAMOT OIL ITALY MPF"PFG" BLO BHT | 10.00 | 10.00 |
| CITRAL DMA | 0.50 | 0.50 |
| CITROFLEX #2 PFIZER | 9.30 | 9.30 |
| CYCLEMAX | 0.50 | 0.50 |
| DAMASCONE, DELTA BHT | 0.10 | 0.10 |
| DIHYDRO MERCENOL | 14.70 | 14.70 |
| GERANIUM BOURBON TYPE | 0.20 | 0.20 |
| HELIONAL | 0.30 | 0.30 |
| ISO E SUPER BHT | 5.00 | 5.00 |
| KHARISMAL | 3.00 | 3.00 |
| LAVANDIN 4066C WO COLOR LMR | 0.40 | 0.40 |
| LINALYL ACET SUPER | 3.00 | 3.00 |
| LYRAL BHT | 4.00 | 4.00 |
| METH BETA NAPH KETONE | 0.50 | 0.50 |
| METH IONONE N BHT | 20.00 | 20.00 |
| MUGUESIA | 0.20 | 0.20 |
| NEBULONE (ELINCS) | 12.00 | 12.00 |
| PEOMOSA | 1.00 | 1.00 |
| POLYSANTOL (ELINCS) MVB | 1.00 | 1.00 |
| PRECYCLEMONE B BHT | 1.00 | 1.00 |
| UNDECAVERTOL MVB | 1.00 | 1.00 |
| VERTOFIX COEUR | 5.00 | 5.00 |
| DIPROPYLENE GLYCOL | — | 5.00 |
| STRUCTURE I | 5.00 | — |
| TOTAL | 100.00 | 100.00 |

*"+" represents a Structure I containing formula; and "−" represents a Structure I non-containing formula.

What is claimed is:
1. A compound of formula:

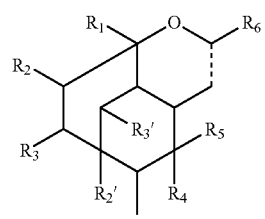

wherein $R_1$ is methyl;
$R_2$ and $R_2'$ are identical and are selected from the group consisting of hydrogen and methyl;

$R_3$ and $R_3'$ are identical and are selected from the group consisting of hydrogen and methyl;

$R_4$ and $R_5$ are independently selected from the group consisting of hydrogen and methyl; and $R_6$ is selected from the group consisting of methyl, ethyl, and isopropyl, and wherein the broken line represents a single or double bond.

2. The compound of claim 1, wherein the compound is 4,6,11-trimethyl-5-oxa-tricyclo[6.2.2.0*4,9*]dodec-6-ene.

3. The compound of claim 1, wherein the compound is 4,6,11-trimethyl-5-oxa-tricyclo[6.2.2.0*4,9*]dodecane.

4. A method of improving, enhancing or modifying a fragrance formulation through the addition of an olfactory acceptable amount of a compound of formula:

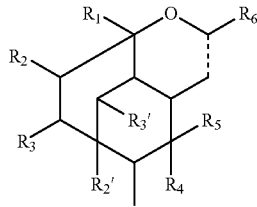

wherein $R_1$ is methyl;

$R_2$ and $R_2'$ are identical and are selected from the group consisting of hydrogen and methyl;

$R_3$ and $R_3'$ are identical and are selected from the group consisting of hydrogen and methyl;

$R_4$ and $R_5$ are independently selected from the group consisting of hydrogen and methyl; and $R_6$ is selected from the group consisting of methyl, ethyl, and isopropyl, and wherein the broken line represents a single or double bond.

5. The method of claim 4, wherein the compound is 4,6,11-trimethyl-5-oxa-tricyclo[6.2.2.0*4,9*]dodec-6-ene.

6. The method of claim 4, wherein the compound is 4,6,11-trimethyl-5-oxa-tricyclo[6.2.2.0*4,9*]dodecane.

7. The method of claim 4, wherein the fragrance formulation is incorporated into a product selected from the group consisting of a perfume, a cologne, a toilet water, a cosmetic product, a personal care product, a fabric care product, a cleaning product, and an air freshener.

8. The method of claim 7, wherein the cleaning product is selected from the group consisting of a detergent, a dishwashing composition, a scrubbing compound, and a window cleaner.

9. The method of claim 4, wherein the olfactory acceptable amount is from about 0.05 to about 35 weight percent of the fragrance formulation.

10. The method of claim 4, wherein the olfactory acceptable amount is from about 0.5 to about 25 weight percent of the fragrance formulation.

11. The method of claim 4, wherein the olfactory acceptable amount is from about 1 to about 10 weight percent of the fragrance formulation.

12. A fragrance composition comprising a compound of formula:

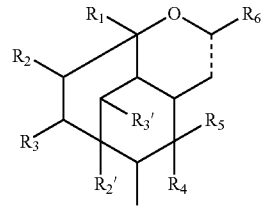

wherein $R_1$ is methyl;

$R_2$ and $R_2'$ are identical and are selected from the group consisting of hydrogen and methyl;

$R_3$ and $R_3'$ are identical and are selected from the group consisting of hydrogen and methyl;

$R_4$ and $R_5$ are independently selected from the group consisting of hydrogen and methyl; and $R_6$ is selected from the group consisting of methyl, ethyl, and isopropyl, and wherein the broken line represents a single or double bond.

13. The fragrance composition of claim 12, wherein the compound is 4,6,11-trimethyl-5-oxa-tricyclo[6.2.2.0*4,9*]dodec-6-ene.

14. The fragrance composition of claim 12, wherein the compound is 4,6,11-trimethyl-5-oxa-tricyclo[6.2.2.0*4,9*]dodecane.

15. A fragrance product containing an olfactory acceptable amount of the compound of claim 1.

16. The fragrance product of claim 15, wherein the compound is 4,6,11-trimethyl-5-oxa-tricyclo[6.2.2.0*4,9*]dodec-6-ene.

17. The fragrance product of claim 15, wherein the compound is 4,6,11-trimethyl-5-oxa-tricyclo[6.2.2.0*4,9*]dodecane.

\* \* \* \* \*